US012408975B2

(12) United States Patent
Park et al.

(10) Patent No.: US 12,408,975 B2
(45) Date of Patent: Sep. 9, 2025

(54) RADIO FREQUENCY ABLATION MEDICAL DEVICE

(71) Applicants: UNIVERSITY OF ULSAN FOUNDATION FOR INDUSTRY COOPERATION, Ulsan (KR); THE ASAN FOUNDATION, Seoul (KR)

(72) Inventors: Jung-hoon Park, Gyeonggi-do (KR); Sang-soo Lee, Seoul (KR); Daesung Ryu, Seoul (KR)

(73) Assignees: UNIVERSITY OF ULSAN FOUNDATION FOR INDUSTRY COOPERATION, Ulsan (KR); THE ASAN FOUNDATION, Seoul (KR)

( * ) Notice: Subject to any disclaimer, the term of this patent is extended or adjusted under 35 U.S.C. 154(b) by 615 days.

(21) Appl. No.: 17/807,605

(22) Filed: Jun. 17, 2022

(65) Prior Publication Data
US 2022/0313354 A1  Oct. 6, 2022

Related U.S. Application Data

(63) Continuation of application No. PCT/KR2020/018704, filed on Dec. 18, 2020.

(30) Foreign Application Priority Data

Dec. 19, 2019 (KR) .................. 10-2019-0171200

(51) Int. Cl.
A61B 18/14 (2006.01)
A61B 18/00 (2006.01)
A61F 2/04 (2013.01)

(52) U.S. Cl.
CPC ............ *A61B 18/1492* (2013.01); *A61F 2/04* (2013.01); *A61B 2018/00714* (2013.01);
(Continued)

(58) Field of Classification Search
CPC ............ A61B 18/1492; A61B 18/1206; A61B 2018/00577; A61B 2018/00702
See application file for complete search history.

(56) References Cited

U.S. PATENT DOCUMENTS 8,058,771 B2  11/2011  Giordano et al.
8,253,303 B2   8/2012  Giordano et al.
(Continued)

FOREIGN PATENT DOCUMENTS

EP    2559995 B1 * 7/2013 ............... G01J 5/10
JP    2013-541987 A    11/2013
(Continued)

OTHER PUBLICATIONS

International Search Report issued Apr. 14, 2021 in PCT/KR2020/018704, filed on Dec. 18, 2020, 7 pages.

Primary Examiner — Linda C Dvorak
Assistant Examiner — Abigail Bock
(74) Attorney, Agent, or Firm — Oblon, McClelland, Maier &Neustadt, L.L.P.

(57) ABSTRACT

A radio frequency ablation medical device includes a guide wire; a catheter configured to be movable to a lesion site of a tissue along the guide wire and having at least one electrode configured to generate heat according to an application of power; and a stent configured to be unfolded when protruding out of the catheter through an end portion of the catheter or recaptured in the end portion of the catheter when entering an inside of the catheter. The stent serves to transfer heat generated by the electrode to the lesion site in an unfolded state when getting out of the catheter.

9 Claims, 6 Drawing Sheets

(52) U.S. Cl.
CPC ............... *A61B 2018/00732* (2013.01); *A61B 2018/1475* (2013.01); *A61B 2562/0271* (2013.01)

(56) References Cited

U.S. PATENT DOCUMENTS

| | | |
|---|---|---|
| 8,546,996 B2 | 10/2013 | Messerly et al. |
| 8,704,425 B2 | 4/2014 | Giordano et al. |
| 8,749,116 B2 | 6/2014 | Messerly et al. |
| 8,779,648 B2 | 7/2014 | Giordano et al. |
| 8,951,248 B2 | 2/2015 | Messerly et al. |
| 8,956,349 B2 | 2/2015 | Aldridge et al. |
| 8,986,302 B2 | 3/2015 | Aldridge et al. |
| 9,039,695 B2 | 5/2015 | Giordano et al. |
| 9,050,093 B2 | 6/2015 | Aldridge et al. |
| 9,060,775 B2 | 6/2015 | Wiener et al. |
| 9,060,776 B2 | 6/2015 | Yates et al. |
| 9,072,539 B2 | 7/2015 | Messerly et al. |
| 9,089,360 B2 | 7/2015 | Messerly et al. |
| 9,168,054 B2 | 10/2015 | Turner et al. |
| 9,504,855 B2 | 11/2016 | Messerly et al. |
| 9,623,237 B2 | 4/2017 | Turner et al. |
| 9,770,353 B2 | 9/2017 | Shin et al. |
| 9,795,808 B2 | 10/2017 | Messerly et al. |
| 10,022,567 B2 | 7/2018 | Messerly et al. |
| 10,022,568 B2 | 7/2018 | Messerly et al. |
| 10,201,382 B2 | 2/2019 | Wiener et al. |
| 10,263,171 B2 | 4/2019 | Wiener et al. |
| 10,265,117 B2 | 4/2019 | Wiener et al. |
| 10,335,614 B2 | 7/2019 | Messerly et al. |
| 10,441,345 B2 | 10/2019 | Aldridge et al. |
| 2009/0143777 A1 | 6/2009 | Pacey et al. |
| 2010/0036405 A1 | 2/2010 | Giordano et al. |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087256 A1 | 4/2011 | Wiener et al. |
| 2012/0078139 A1 | 3/2012 | Aldridge et al. |
| 2012/0123458 A1 | 5/2012 | Giordano et al. |
| 2012/0265196 A1 | 10/2012 | Turner et al. |
| 2012/0310262 A1 | 12/2012 | Messerly et al. |
| 2012/0310263 A1 | 12/2012 | Messerly et al. |
| 2012/0310264 A1 | 12/2012 | Messerly et al. |
| 2013/0035706 A1 | 2/2013 | Giordano et al. |
| 2013/0035707 A1 | 2/2013 | Giordano et al. |
| 2015/0133927 A1 | 5/2015 | Shin et al. |
| 2015/0182251 A1 | 7/2015 | Messerly et al. |
| 2015/0182276 A1 | 7/2015 | Wiener et al. |
| 2015/0182277 A1 | 7/2015 | Wiener et al. |
| 2015/0196318 A1 | 7/2015 | Messerly et al. |
| 2015/0327883 A1 | 11/2015 | Messerly et al. |
| 2015/0328484 A1 | 11/2015 | Messerly et al. |
| 2015/0340586 A1 | 11/2015 | Wiener et al. |
| 2016/0089533 A1 | 3/2016 | Turner et al. |
| 2017/0095267 A1 | 4/2017 | Messerly et al. |
| 2017/0231694 A1 | 8/2017 | Mathur et al. |
| 2018/0116706 A9 | 5/2018 | Wiener et al. |
| 2018/0168714 A9 | 6/2018 | Wiener et al. |
| 2019/0282292 A1 | 9/2019 | Wiener et al. |
| 2020/0078609 A1 | 3/2020 | Messerly et al. |

FOREIGN PATENT DOCUMENTS

| | | |
|---|---|---|
| KR | 10-0472737 B1 | 3/2005 |
| KR | 10-2010-0105365 A | 9/2010 |
| KR | 10-2013-0140954 A | 12/2013 |

\* cited by examiner

RADIO FREQUENCY ABLATION MEDICAL DEVICE

FIELD OF THE DISCLOSURE

The disclosure relates to a radio frequency ablation medical device.

RELATED ART

Recently, various procedures have been performed using a method of applying high frequencies of various outputs to a human body at specific intervals.

For example, various types of treatment, such as high frequency therapy for liver cancer, which applies high frequency heating to necrotic tumor cells in the liver, and high frequency therapy, which is used to treat muscle pain and joint pain by applying a radio frequency current to the human body to generate heat inside the human body, have been performed.

As catheters for radio frequency ablation that are commercially available in clinical practice, there are Habib EndoHBP (EMcision, London, UK) and ELRA RFA catheters (Starmed, Goyang, Korea). The Habib catheter is an 8Fr bipolar catheter, and can be inserted into an endoscope along a guide wire in the form in which the Habib catheter has two 8 mm electrodes attached thereto. The ELRA catheter is a 7Fr bipolar catheter, and has four types: 11 mm, 18 mm, 22 mm, and 33 mm.

However, for the treatment of malignant biliary stenosis including biliary tract cancer, the conventional radio frequency ablation (RFA) catheter used for radio frequency ablation (RFA) causes several problems.

For example, when the radio frequency ablation catheter is applied to a curved biliary duct lesion, it may be difficult to uniformly transfer heat to tissues in the biliary tract, thermal ablation may be performed on an unwanted area through the radio frequency ablation catheter, and thermal ablation may not be sufficiently performed on a lesion site. In addition, in the case of the bipolar catheter having a diameter of 7Fr or 8Fr, since the catheter may not pass through the severe stenosis, treatment using the catheter may be difficult.

RELATED ART DOCUMENT

Korean Patent Laid-Open Publication No. 10-2010-0105365 (published on Sep. 29, 2010)

SUMMARY

Embodiments of the present disclosure provide a radio frequency ablation medical device capable of uniformly transferring heat to a tissue in a biliary tract and controlling an ablation range.

In accordance with an embodiment of the present disclosure, there is provided a radio frequency ablation medical device including: a guide wire; a catheter configured to be movable to a lesion site of a tissue along the guide wire and having at least one electrode configured to generate heat according to an application of power; and a stent configured to be unfolded when protruding out of the catheter through an end portion of the catheter or recaptured in the end portion of the catheter when entering an inside of the catheter, the stent serving to transfer heat generated by the electrode to the lesion site in an unfolded state when getting out of the catheter.

The catheter may include: a support tube configured to be movable along the guide wire; a peak tube supported by the support tube, wherein the peak tube is disposed in the stent so that the stent surrounds the peak tube; and a moving tube configured to accommodate at least a portion of the stent therein, the moving tube being movable along the support tube to adjust a length of the stent protruding out of the catheter.

The radio frequency ablation medical device may further include: a thermal detection sensor for measuring an electrode temperature value of the electrode when the power is applied to the electrode.

The radio frequency ablation medical device may further include a radio frequency generator for applying power to the electrode, wherein the radio frequency generator may include: a power supply for applying power to the electrode; a temperature input unit configured to receive a specific temperature value of the electrode; a time input unit configured to receive a specific heating time during which the electrode is heated; an electrode temperature receiver for receiving the electrode temperature value of the electrode from the thermal detection sensor; and a temperature control unit configured to determine whether the electrode temperature value exceeds the specific temperature value or a heating time of the electrode exceeds the specific heating time and control the power supply to cut off the application of power to the electrode when it is determined that the electrode temperature value exceeds the specific temperature value or the heating time of the electrode exceeds the specific heating time.

The radio frequency ablation medical device may further include: a radio frequency generator for applying power to the electrode, wherein the radio frequency generator controls the electrode temperature value of the electrode depending on an expansion length of the unfolded stent so that the electrode temperature value received from the thermal detection sensor satisfies a preset temperature compensation range.

The temperature compensation range may be a temperature compensation range of the electrode for keeping a temperature of the unfolded stent constant when the expansion length is changed.

The stent may be provided in a form of a cylindrical mesh which compresses and surrounds the peak tube by pressing of the moving tube in a space between the peak tube and the moving tube of the catheter.

The radio frequency ablation medical device may further include: a pusher connected to the moving tube, wherein the stent is unfolded from the peak tube to be in close contact with the lesion site when the pressing of the moving tube is released according to a movement of the moving tube in one direction in response to a pull operation of the pusher, and the stent is recaptured into the catheter by the pressing of the moving tube according to a movement of the moving tube in the other direction in response to a push operation of the pusher.

The radio frequency ablation medical device may further include: a radio frequency generator for applying power to the electrode, wherein the radio frequency generator further includes a temperature compensation calculator that calculates a temperature compensation range of the electrode for keeping a temperature of the stent constant depending on an expansion length of the stent.

After determining whether the electrode temperature satisfies the temperature compensation range, the temperature controller may control the temperature of the electrode so that the electrode temperature satisfies the temperature compensation range.

The radio frequency ablation medical device may further include: a thermal image sensor for measuring a temperature for each length section of the stent.

The radio frequency ablation medical device may further include: a radio frequency generator that applies power to the electrode, wherein the radio frequency generator receives temperature information for each length section of the stent from the thermal image sensor, and controls the temperature of the electrode so that the temperature for each length section of the stent satisfies a preset temperature section range.

According to the embodiments of the present disclosure, it is possible to perform radio frequency ablation using a stent widely used for nonvascular stenosis disease, uniformly transfer heat to a lesion site of a tissue in a biliary tract, and control an ablation range for the lesion site.

In addition, the embodiments of the present disclosure can be applied to various non-vascular organs that require local thermal ablation, including a biliary tract.

DESCRIPTION OF EXEMPLARY EMBODIMENTS

Figure 1:
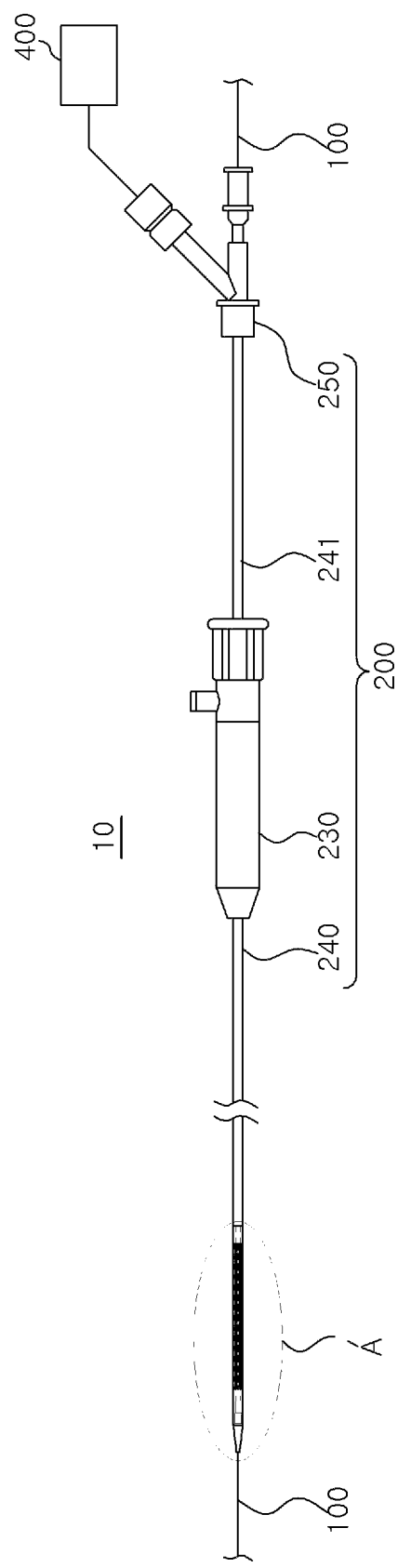
FIG. 1 is a configuration diagram illustrating a radio frequency ablation medical device according to an embodiment of the present disclosure.

Hereinafter, a configuration and operation according to an embodiment of the present disclosure will be described in detail with reference to the accompanying drawings. The following description is one of many claimable aspects of the disclosure and may form part of the detailed description of the disclosure. However, in describing the present disclosure, detailed descriptions of known configurations or functions may be omitted to clarify the present disclosure.

The present disclosure may make various changes and include various embodiments, and specific embodiments will be illustrated in the drawings and described in the detailed description. However, the present disclosure is not limited to a specific embodiment, and it should be understood that the present disclosure includes all changes, equivalents, or substitutes included in the spirit and scope thereof.

Terms including ordinal numbers, such as first and second, may be used for describing various elements, but the corresponding elements are not limited by these terms. These terms are only used for the purpose of distinguishing one element from another element. When an element is referred to as being 'connected' to or 'accessed' by another element, it should be understood that the element may be directly connected to or accessed by the other element, but that other elements may exist in the middle. The terms used in the present disclosure are only used for describing specific embodiments, and are not intended to limit the present disclosure. Singular expressions include plural expressions unless the context clearly indicates otherwise.

Figure 2:
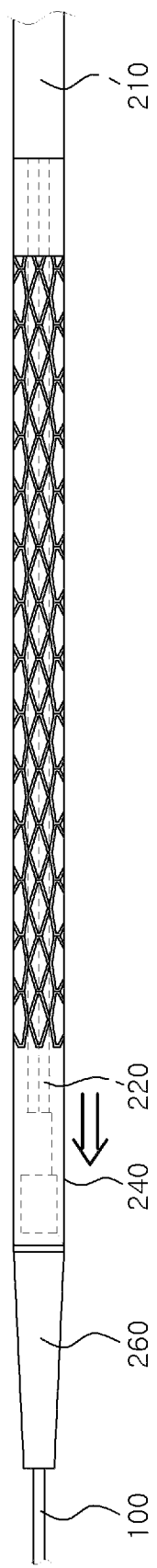
FIG. 2 is an enlarged view of part A of FIG. 1.
Figure 3:
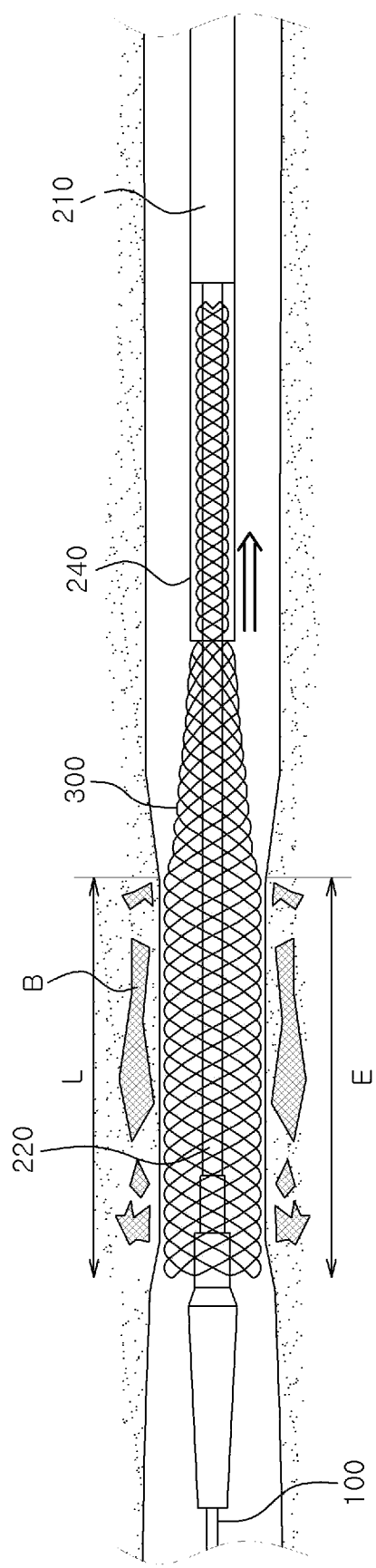
FIG. 3 is a state diagram illustrating a state in which a stent of the radio frequency ablation medical device according to the embodiment of the present disclosure is unfolded at a lesion site.
Figure 4:
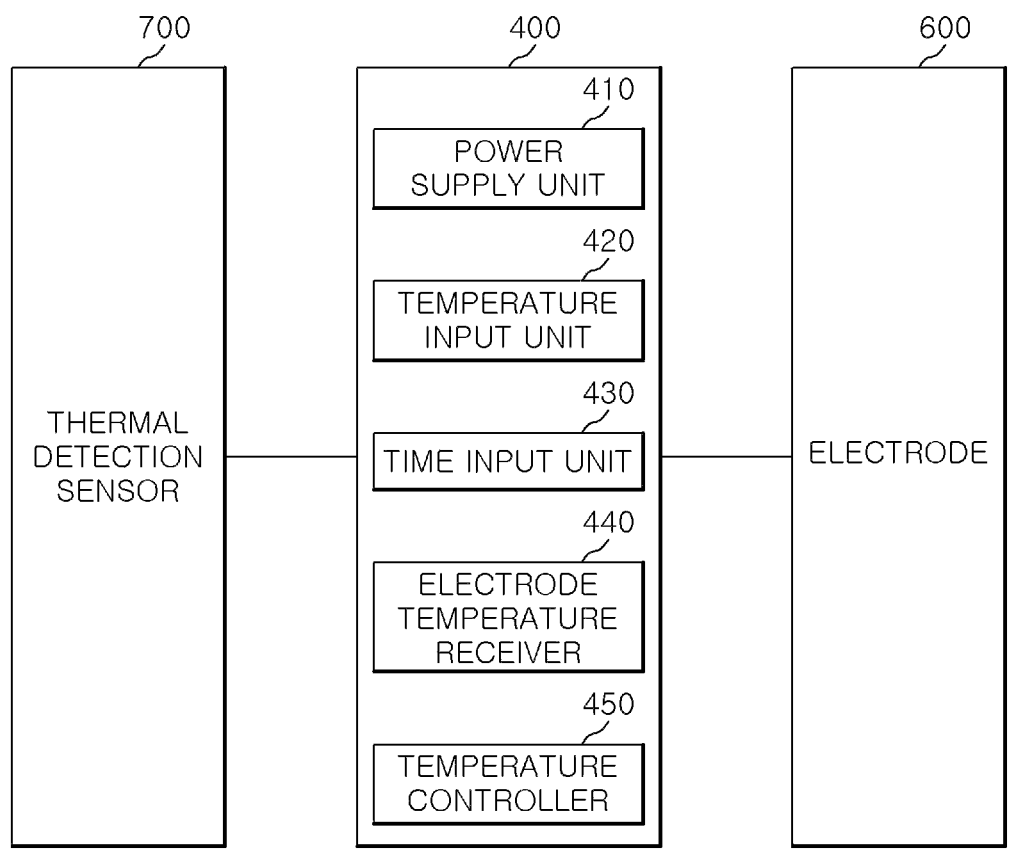
FIG. 4 is a block diagram illustrating a control flow of a radio frequency generator of the radio frequency ablation medical device according to the embodiment of the present disclosure.

FIG. 1 is a configuration diagram illustrating a radio frequency ablation medical device according to an embodiment of the present disclosure, FIG. 2 is an enlarged view of part A of FIG. 1, FIG. 3 is a state diagram illustrating a state in which a stent of the radio frequency ablation medical device according to the embodiment of the present disclosure is unfolded at a lesion site, and FIG. 4 is a block diagram illustrating a control flow of a radio frequency generator of the radio frequency ablation medical device according to the embodiment of the present disclosure.

As illustrated in FIGS. 1 to 4, a radio frequency ablation medical device 10 according to the embodiment of the present disclosure may include a guide wire 100, a catheter 200, a stent 300, a thermal detection sensor 700, and a radio frequency generator 400.

Specifically, the guide wire 100 may be provided in the form of a wire for guiding a catheter 200 to a lesion site L generated in a patient's tissue (e.g., tissue in a biliary tract). The guide wire 100 may be mounted in a manner that penetrates through the catheter 200, and the catheter 200 may move along the guide wire 100.

The catheter 200 may be moved to the lesion site L of the tissue along the guide wire 100. In a state where the catheter 200 is positioned at the lesion site L of the tissue, thermal ablation may be performed on a lesion B of the tissue using heat provided through the stent 300. An electrode 600 for providing heat to the stent 300 may be provided in a front end portion of the catheter 200.

The catheter 200 may include a support tube 210, a peak tube 220, a hub 230, a moving tube 240, and a pusher 250. The support tube 210 may be provided in the form of a hollow tube movable along the guide wire 100. A front end of the support tube 210 may be coupled to the peak tube 220, and a rear end of the support tube 210 may be coupled to the hub 230.

The peak tube 220 may be provided in the form of a hollow tube movable along the guide wire 100. A stent 300 may be mounted on the circumference of the peak tube 220. A conical guide tip 260 may be coupled to the front end of the peak tube 220, and a rear end of the peak tube 220 may be coupled to the support tube 210.

The peak tube 220 may be provided with an electrode 600. The electrode 600 may be electrically connected to the radio frequency generator 400. The electrode 600 may receive power required for heat generation from the radio frequency generator 400. The electrode 600 may generate heat and provide the heat to the stent 300. The electrode temperature generated from the electrode 600 may satisfy the range of 70° C. to 100° C.

In the present embodiment, at least one or more (for example, 3 to 5) electrodes 600 are disposed spaced apart from the front end portion of the catheter 200 (for example, the front end portion of the peak tube 220), but is not limited thereto, and in addition to the electrode, various types of heating elements capable of heating the stent 300 through the heat generation may be provided in the front end portion of the catheter 200. As the heating element, a hot wire capable of generating heat may be used.

The hub 230 may be coupled to the rear end of the support tube 210. A support tube 241 may penetrate through the hub 230 to be connected to the moving tube 240. The support tube 241 may be provided in the form of a hollow tube connecting the moving tube 240 and the pusher 250. The guide wire 100 may penetrate through the support tube 241. When a user pulls or pushes the pusher 250, the support tube 241 may transmit an operating force of the pusher 250 to the moving tube 240.

The moving tube 240 may be provided in the form of a tube in which at least a portion (e.g., front end portion) thereof surrounds the stent 300. The moving tube 240 may be connected to the pusher 250 via the support tube 241. Accordingly, during the pull or push operation of the pusher 250, the moving tube 240 may move backward or forward along the support tube 210. The moving tube 240 may be made of a material capable of blocking heat conduction.

In particular, when the moving tube 240 is moved in a rearward direction (a direction in which the pusher is pulled) along the support tube 210, the stent 300 may be unfolded out from the moving tube 240. In this case, an expansion length E of the stent 300 in which the stent 300 is unfolded may be controlled in proportion to the moving distance of the moving tube 240 moving in the rear direction. Further, when the moving tube 240 is moved in a forward direction (a direction in which the pusher is pushed) along the support tube 210, the stent 300 may be recaptured by the moving tube 240.

The stent 300 may be provided in the form of a cylindrical mesh. The stent 300 may be unfolded to be controllable in length in the end portion of the catheter 200 or may be recaptured into the end portion of the catheter 200.

For example, when the stent 300 may be pressed by the moving tube 240, the stent 300 is located in a space between the peak tube 220 and the moving tube 240 of the catheter 200, and therefore, may be maintained in a compressed state while surrounding the peak tube 220. When the pressure of the moving tube 240 with respect to the stent 300 is released, the stent 300 may be restored to the original form of the cylindrical mesh while being expanded. When the stent 300 is unfolded from the end portion of the catheter 200, the stent 300 may provide heat generated from the electrode 600 to the lesion site L.

Accordingly, during the pull operation of the pusher 250, when the pressure of the moving tube 240 with respect to the stent 300 is released according to the rearward movement of the moving tube 240, the stent 300 may be unfolded from the front end portion of the peak tube 220 so as to be in close contact with the lesion site L. During the push operation of the pusher 250, when the moving tube 240 is pressed against the stent 300 according to the forward movement of the moving tube 240, the stent 300 may be recaptured into the space between the moving tube 240 and the support tube 210 of the catheter 200.

The thermal detection sensor 700 may include a temperature sensor capable of measuring an electrode temperature generated from the electrode 600. Since the thermal detection sensor 700 is installed in contact with the electrode 600 or installed adjacent to the electrode 600, it is possible to measure the electrode temperature generated from the electrode 600. The information on the electrode temperature value of the electrode 600 measured by the thermal detection sensor 700 may be applied to the radio frequency generator 400.

The radio frequency generator 400 may be electrically connected to the electrode 600 to apply power to the electrode 600. The radio frequency generator 400 may include a power supply unit 410, a temperature input unit 420, a time input unit 430, an electrode temperature receiver 440, and a temperature controller 450.

The power supply unit 410 may receive power from an external power supply, and provide at least a portion of the received power to the electrode 600. The temperature input unit 420 may receive a specific temperature of the electrode 600 from the user. Here, the specific temperature may be understood as a maximum temperature of the electrode 600 at which the application of power to the electrode 600 is permitted.

The time input unit 430 may receive a specific time at which the heating of the electrode 600 from the user is performed. Here, the specific time may be understood as a maximum time during which the application of power to the electrode 600 is permitted. The electrode temperature receiver 440 may receive an electrode temperature value of the electrode 600 measured from the thermal detection sensor 700.

When the specific temperature provided through the temperature input unit 420 exceeds the electrode temperature value applied from the electrode temperature receiver 440, the temperature controller 450 may control the power supply unit 410 so that the application of power to the electrode 600 is automatically cut off. For example, when the specific temperature provided through the temperature input unit 420 is 80° C. and the electrode temperature value applied from the electrode temperature receiver 440 is 75° C., the temperature controller 450 may apply power to the electrode 600 until the electrode temperature value reaches 80° C., and when the electrode temperature value exceeds 80° C., the temperature controller 450 may cut off the application of power to the electrode 600. In this way, when the application of power to the electrode 600 is controlled based on a specific temperature, damage to an organ due to an excessive increase in temperature may be prevented in advance.

In addition, when the heating time of the electrode 600 exceeds a specific time provided through the time input unit 430, the temperature controller 450 may control the power supply unit 410 to automatically cut off the application of power to the electrode 600. For example, when the specific time provided through the time input unit 430 is 1 minute, the temperature controller 450 may apply power to the electrode 600 until the heating time of the electrode 600 becomes 1 minute, and when the heating time of the electrode 600 exceeds 1 minute, the temperature controller 450 may cut off the application of power to the electrode 600.

Meanwhile, when power is supplied to the electrode 600 by the radio frequency generator 400, even if the mass of the stent 300 itself to which the heat generated from the electrode 600 is transferred is constant, since the expansion (unfolded) portion of the stent 300 is in contact with the patient's lesion site L, considering a patient's body having a larger specific heat than that of the stent 300, when the expansion length E of the stent 300 is long, the amount of heat required to reach a predetermined target temperature (e.g., a specific temperature) is required more than when the expansion length E of the stent 300 is relatively small. Therefore, it is necessary to correct the relationship between the expansion length E of the stent 300 and the amount of heat generated from the electrode 600.

Accordingly, the radio frequency generator 400 may control the temperature of the electrode 600 in accordance with the change in the expansion length E at which the stent 300 is unfolded, so that the electrode temperature applied from the thermal detection sensor 700 satisfies the preset temperature compensation range.

Here, the temperature compensation range may be the temperature range of the electrode 600 set to keep the temperature of the stent 300 constant even if the expansion length E of the stent 300 changes. The temperature compensation range may be preset through data calculated through a temperature relationship of the electrode 600 according to the change in the expansion length E.

For example, if the standard temperature of the electrode 600 required for thermal ablation of the lesion site L is 80° C. when the expansion length E of the stent 300 is 20 mm, the temperature compensation range of the electrode 600 required for thermal ablation of the lesion site L may be preset in the range of 80.5° C. to 81.5° C. when the expansion length (E) of the stent 300 is 30 mm through the data on the temperature relationship of the electrode 600 according to the change of the expansion length E.

After all, for the thermal ablation of the lesion site L, when the expansion length E of the stent 300 is adjusted from 20 mm to 30 mm, the radio frequency generator 400 may heat or lower the temperature of the electrode 600 based on the expansion length E adjusted to 30 mm so that the electrode temperature applied from the thermal detection sensor 700 satisfies the preset temperature compensation range of 80.5° C. to 81.5° C.

Figure 5:
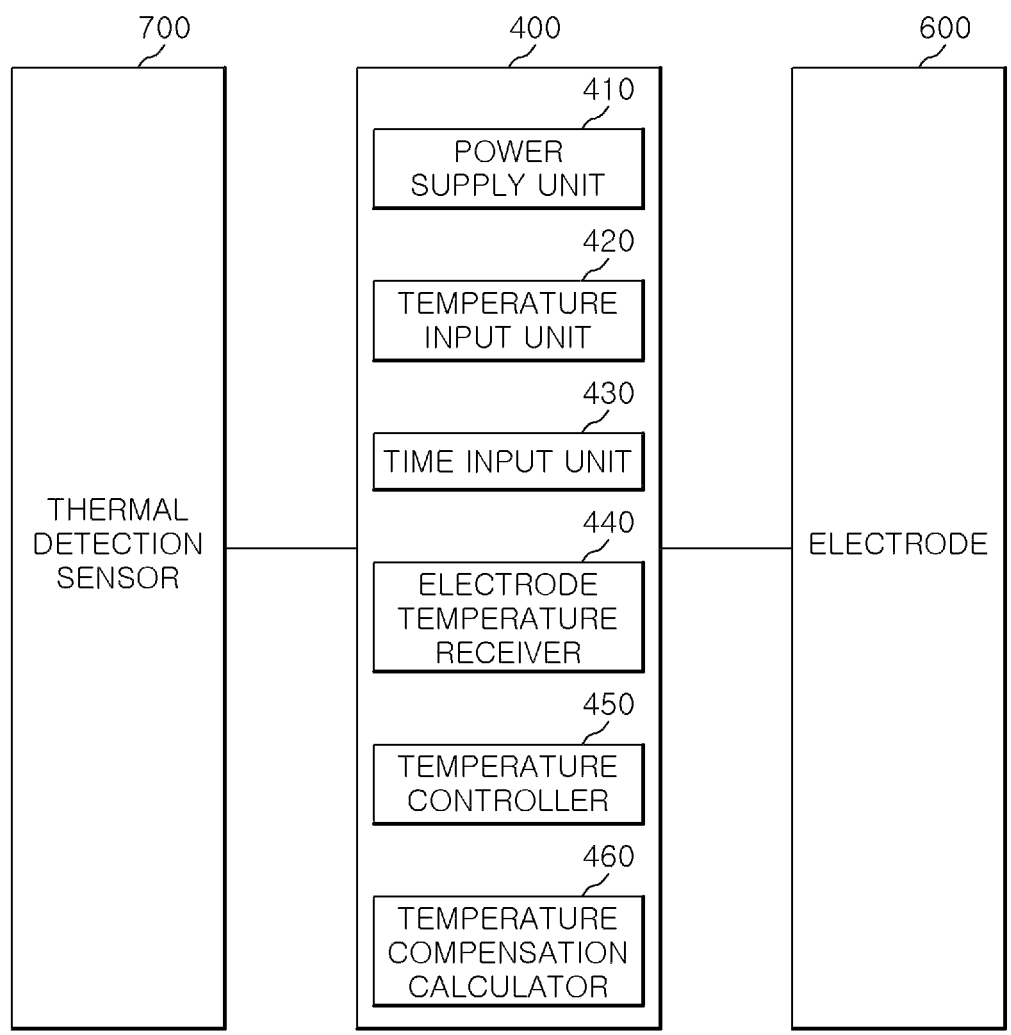
FIG. 5 is a block diagram illustrating a control flow of a radio frequency generator of a radio frequency ablation medical device according to a modification of the present disclosure.

FIG. 5 is a block diagram illustrating a control flow of a radio frequency generator of a radio frequency ablation medical device according to a modification of the present disclosure.

As illustrated in FIG. 5, according to a modification of the present disclosure, the radio frequency generator 400 may include a power supply unit 410, a temperature input unit 420, a time input unit 430, an electrode temperature receiver 440, a temperature compensation calculator 460, and a temperature controller 450. Here, the configurations other than the temperature controller 450 and the temperature compensation calculator 460 correspond to the configurations described above, and therefore, a detailed description thereof will be omitted.

The temperature compensation calculator 460 may calculate the temperature compensation range of the electrode 600 through data on the temperature relationship of the electrode 600 according to the change in the expansion length E in order to keep the temperature of the stent 300 constant according to the change of the expansion length E.

After determining whether the electrode temperature satisfies the temperature compensation range calculated by the temperature compensation calculator 460, the temperature controller 450 may control the temperature of the electrode 600 so that the electrode temperature satisfies the temperature compensation range.

For example, when the expansion length E of the stent 300 is adjusted from 20 mm to 30 mm, the radio frequency generator 400 may heat or lower the temperature of the electrode 600 based on the expansion length E adjusted to 30 mm so that the electrode temperature applied from the thermal detection sensor 700 satisfies the temperature compensation range of 80.5° C. to 81.5° C. calculated by the temperature compensation calculator 460.

Figure 6:
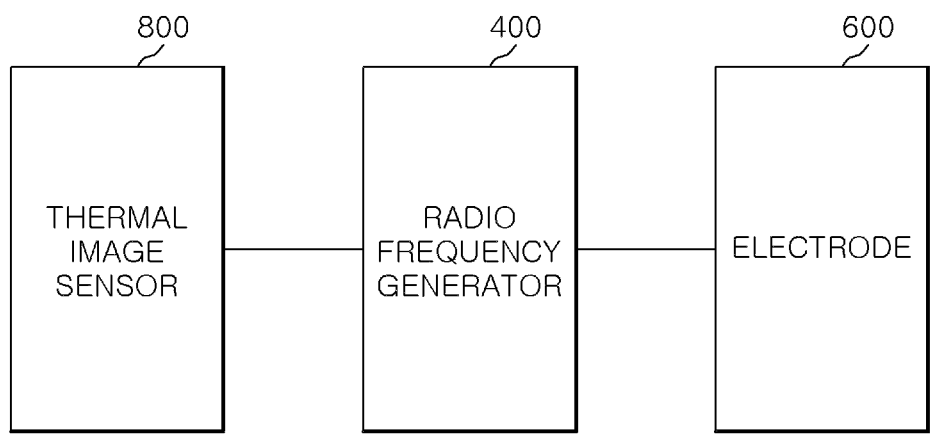
FIG. 6 is a block diagram illustrating a control flow of a radio frequency generator of a radio frequency ablation medical device according to another embodiment of the present disclosure.

FIG. 6 is a block diagram illustrating a control flow of a radio frequency generator of a radio frequency ablation medical device according to another embodiment of the present disclosure.

As illustrated in FIG. 6, the radio frequency ablation medical device 10 according to the embodiment of the present disclosure may further include a thermal image sensor 800.

The thermal image sensor 800 may measure the temperature for each length section of the stent 300. Here, the temperature for each length section may be understood as an average value of temperatures measured in a plurality of sections arbitrarily dividing the stent 300 along the longitudinal direction. The information on the temperature for each length section of the stent 300 measured through the thermal image sensor 800 may be applied to the radio frequency generator 400.

The radio frequency generator 400 may control the temperature of the electrode 600 so that the temperature for each length section of the stent 300 applied from the thermal image sensor 800 satisfies a preset temperature section range.

For example, when the preset temperature section ranges from 85° C. to 86° C., the temperature for each length section of the stent 300 obtained from the thermal image sensor 800 is 83° C., the radio frequency generator 400 may heat the temperature of the electrode 600 so that the temperature for each length section satisfies the preset temperature section ranging from 85° C. to 86° C.

Through this, the temperature of the stent required for thermal ablation to the lesion site L of the tissue may be kept constant, and as a result, uniform heat transfer to the lesion site L may be possible.

As described above, the present disclosure has excellent advantages such as performing that radio frequency ablation using a stent widely used for nonvascular stenosis disease, uniformly transferring heat to the lesion site of the tissue in the biliary tract, controlling the ablation range for the lesion site, and being applied to various non-vascular organs that require local thermal ablation, including the biliary tract.

The embodiments described above are merely some examples illustrating the present technical spirit, and the technical scope of the present disclosure is not limited by the embodiments. It will be understood by those skilled in the art that various changes, modifications and substitutions can be made without departing from the technical scope of the present disclosure, and all such implementations should be considered to fall within the scope of the present technical spirit.

(National R&D project supporting the present invention)
(Project number) 1711112394
(Project unique number) 2020R1A2C2003604
(Ministry name) Ministry of Science and Technology Information and Communication
(Name of project management (specialized) institution): Specialized institution: National Research Foundation of Korea
(Research project name) Personal basic research project (middle-level research)
(Research project name) Development of next-generation radio frequency ablation medical device for treatment of malignant bile duct stenosis
(Contribution Rate) 1/1
(Name of organization performing task) Ulsan University Industry-Academic Cooperation Foundation
(Research Period) 2020.03.01 to 2023.02.28

What is claimed is:
1. A radio frequency ablation medical device comprising:
a guide wire;

a catheter configured to be movable to a lesion site of a tissue along the guide wire and having at least one electrode configured to generate heat according to an application of power;

a stent configured to be unfolded when protruding out of the catheter through an end portion of the catheter or recaptured in the end portion of the catheter when entering an inside of the catheter, the stent serving to transfer heat generated by the electrode to the lesion site in an unfolded state when getting out of the catheter;

a thermal detection sensor for measuring an electrode temperature value of the electrode when the power is applied to the electrode; and a radio frequency generator for applying power to the electrode, wherein the radio frequency generator controls the electrode temperature value of the electrode depending on an expansion length of the unfolded stent so that the electrode temperature value received from the thermal detection sensor satisfies a preset temperature compensation range.

2. The radio frequency ablation medical device of claim 1, wherein the catheter includes:

a support tube configured to be movable along the guide wire;

a peak tube supported by the support tube, wherein the peak tube is disposed in the stent so that the stent surrounds the peak tube; and a moving tube configured to accommodate at least a portion of the stent therein, the moving tube being movable along the support tube to adjust a length of the stent protruding out of the catheter.

3. The radio frequency ablation medical device of claim 1, wherein the radio frequency generator includes:

a power supply for applying power to the electrode;

a temperature input unit configured to receive a specific temperature value of the electrode;

a time input unit configured to receive a specific heating time during which the electrode is heated;

an electrode temperature receiver for receiving the electrode temperature value of the electrode from the thermal detection sensor; and a temperature control unit configured to determine whether the electrode temperature value exceeds the specific temperature value or a heating time of the electrode exceeds the specific heating time and control the power supply to cut off the application of power to the electrode when it is determined that the electrode temperature value exceeds the specific temperature value or the heating time of the electrode exceeds the specific heating time.

4. The radio frequency ablation medical device of claim 1, wherein the temperature compensation range is a temperature compensation range of the electrode for keeping a temperature of the unfolded stent constant when the expansion length is changed.

5. The radio frequency ablation medical device of claim 1, wherein the stent is provided in a form of a cylindrical mesh which compresses and surrounds the peak tube by pressing of the moving tube in a space between the peak tube and the moving tube of the catheter.

6. The radio frequency ablation medical device of claim 5, further comprising:

a pusher connected to the moving tube, wherein the stent is unfolded from the peak tube to be in close contact with the lesion site when the pressing of the moving tube is released according to a movement of the moving tube in one direction in response to a pull operation of the pusher, and the stent is recaptured into the catheter by the pressing of the moving tube according to a movement of the moving tube in the other direction in response to a push operation of the pusher.

7. A radio frequency ablation medical device comprising:

a guide wire;

a catheter configured to be movable to a lesion site of a tissue along the guide wire and having at least one electrode configured to generate heat according to an application of power;

a stent configured to be unfolded when protruding out of the catheter through an end portion of the catheter or recaptured in the end portion of the catheter when entering an inside of the catheter, the stent serving to transfer heat generated by the electrode to the lesion site in an unfolded state when getting out of the catheter;

a thermal detection sensor for measuring an electrode temperature value of the electrode when the power is applied to the electrode; and a radio frequency generator for applying power to the electrode, wherein the radio frequency generator further includes a temperature compensation calculator that calculates a temperature compensation range of the electrode for keeping a temperature of the stent constant depending on an expansion length of the stent.

8. The radio frequency ablation medical device of claim 7, wherein, after determining whether the electrode temperature satisfies the temperature compensation range, the temperature controller controls the temperature of the electrode so that the electrode temperature satisfies the temperature compensation range.

9. A radio frequency ablation medical device comprising:

a guide wire;

a catheter configured to be movable to a lesion site of a tissue along the guide wire and having at least one electrode configured to generate heat according to an application of power;

a stent configured to be unfolded when protruding out of the catheter through an end portion of the catheter or recaptured in the end portion of the catheter when entering an inside of the catheter, the stent serving to transfer heat generated by the electrode to the lesion site in an unfolded state when getting out of the catheter;

a thermal image sensor for measuring a temperature for each length section of the stent; and a radio frequency generator that applies power to the electrode, wherein the radio frequency generator receives temperature information for each length section of the stent from the thermal image sensor, and controls the temperature of the electrode so that the temperature for each length section of the stent satisfies a preset temperature section range.

* * * * *